United States Patent [19]

Rüegg et al.

[11] Patent Number: 5,220,284
[45] Date of Patent: Jun. 15, 1993

[54] METHOD AND DEVICE FOR MEASURING THE CONCENTRATION OF PARTICLES IN A GAS BY IONIZATION OF THE PARTICLES

[75] Inventors: Walter Rüegg, Endingen; John A. Byatt, Klingnau, both of Switzerland

[73] Assignee: Asea Brown Boveri Ltd., Baden, Switzerland

[21] Appl. No.: 850,813

[22] Filed: Mar. 13, 1992

[30] Foreign Application Priority Data

Mar. 13, 1991 [CH] Switzerland .................. 763/91-0

[51] Int. Cl.$^5$ ........................................ G01N 27/66
[52] U.S. Cl. ..................................... 324/464; 250/382
[58] Field of Search ............... 324/464, 466, 468, 469, 324/470, 465; 250/423 P, 379, 372, 382

[56] References Cited

U.S. PATENT DOCUMENTS

| | | | |
|---|---|---|---|
| 2,898,497 | 8/1959 | Cartnell et al. | 250/379 X |
| 4,837,440 | 6/1989 | Burtscher. | |

FOREIGN PATENT DOCUMENTS

| | | |
|---|---|---|
| 0160888 | 11/1985 | European Pat. Off. |
| 1648902 | 5/1971 | Fed. Rep. of Germany. |
| 3409932 | 5/1985 | Fed. Rep. of Germany. |
| 3422053 | 12/1985 | Fed. Rep. of Germany. |
| 3422054 | 12/1985 | Fed. Rep. of Germany. |
| 3417525 | 1/1986 | Fed. Rep. of Germany. |
| 3515258 | 11/1986 | Fed. Rep. of Germany. |
| 217893A1 | 1/1985 | German Democratic Rep. |

OTHER PUBLICATIONS

Bulletin SEV/USE 80 (1989) 23, Dec. 2, 1989, pp. 1515-1519, H. Burtscher, "Dynamische Messung Von Partikeln Mittels Aerosol—Photomission".
Journal of Applied Physics, 53(5), May 1982, pp. 3787-3791, H. Burtscher, et al., "Probing Aerosols by Photoelectric Charging".
Zeitschrift fur Physikalische Chemie Neue Folge, Bd. 159, Jun. 1988, pp. 129-148, V. W. Robers, et al., "Photo— and Thermoionisation Von Aerosolen".
Central Patent Index, Basis Abstracts Journal Section J. Jan. 1991, 91/049020/07, "Process and Equipment for Measurement of Microparticles in Liq.—in Which Liq. is Gasified and Particles are Charged by . . .".
Soviet Inventions Illustrated, Section E1:Electrical, Mar. 11, 1987, pp. 12, 87-028482/04, "Rapid Monitoring Device E.G. for Pre-Smog Atoms Condition—Has Shutter to Modulate UV Radiation".
Soviet Inventions Illustrated, Section R:Electrical, May 21, 1980, D3569C/15, "Atmosphere Aerosol Sample Extraction Appts.—Has Ioniser Made as UV Light Source with Spiral Mounted On . . .".

Primary Examiner—Jack B. Harvey
Attorney, Agent, or Firm—Oblon, Spivak, McClelland, Maier & Neustadt

[57] ABSTRACT

In a method and a device for measuring the concentration of particles present in a gas, in which a gas stream is guided past a UV light source, the particles are ionized and filtered out and the resulting ionic current is measured, the gas flow required is produced by thermal convection using an internal or external heat source. A suitable internal heat source in this context is, for example, the UV lamp (2) itself, which heats the gas via a radiation absorber (5). The elimination of a mechanical pump reduces the space requirement, power consumption and susceptibility to faults of the measuring arrangement.

9 Claims, 2 Drawing Sheets

METHOD AND DEVICE FOR MEASURING THE CONCENTRATION OF PARTICLES IN A GAS BY IONIZATION OF THE PARTICLES

BACKGROUND OF THE INVENTION

1. Field of the Invention

The invention relates to the field of environmental measurement technology. It relates, in particular, to a method for measuring the concentration of particles present in a gas, in which method the gas with the particles is guided in the form of a gas stream past a UV light source, the particles are ionized by the UV radiation from the UV light source, the ionized particles are filtered out of the gas stream and the ionic current which arises is measured.

It furthermore relates to a device for measuring the concentration of particles present in a gas, comprising
(a) a tubular measuring chamber through which the gas with the particles flows in the form of a gas stream;
(b) at the start of the measuring chamber a UV light source, past which the gas flows, the particles present in the gas being at least partially ionized;
(c) downstream of the UV light source, an electrically conducting ion filter which filters the ionized particles out of the gas stream and releases the electric charges picked up in the process in the form of an electric current to a downstream electronic measuring unit; and
(d) means for producing the flow of the gas through the measuring chamber.

A method of this kind and a device of this kind are disclosed, for example, in U.S. Pat. No. 4,837,440 and an article by H. Burtscher, Bulletin SEV/VSE 80 (1989) 23, 2nd December, pages 1515–1519.

DISCUSSION OF BACKGROUND

Due to the increasing burden imposed on the environment by pollutants released into the air by, for example, oil-fired heating systems or traffic, simple and reliable methods and apparatuses for measuring and monitoring the quality of the air are becoming increasingly important.

Of particular importance are the particles suspended in the air, which can be used to measure the quality of the air for the following reason: each time fossil fuels are burnt, minute particles of carbon ($\gamma < 0.1$ $\mu$m) are produced. When the combustion gas cools, a condensate can form on the surface of these particles and this contains, inter alia, so-called polyaromatic hydrocarbons (PAH). The concentration of these PAH is a good measure of the quality of combustion; it also shows good correlation with other pollutants formed in the case of poor combustion, in particular with CO. By measuring the PAH concentration it is thus also possible to give a verdict on the quality of the air.

A known and recognized method for measuring the PAH concentration is based on the following principle: particles, on the surface of which PAH are present, can be easily ionized by irradiation with UV light (wavelength of, for example, 185 nm). If, after separating off the electrons produced upon ionization, the gas containing such ionized particles is pumped through an electrically conducting (ion) filter, it is possible to measure the ionic current and hence the concentration of PAH particles.

One disadvantage of this known measurement method is the fact that a pump is provided to produce the gas stream. A pump is technically complicated, expensive, of limited life (wear, fouling), generates noise and vibrations and requires a large amount of space and electric power.

SUMMARY OF THE INVENTION

It is therefore the object of the present invention to indicate a method and a device for measuring the particle concentration which avoid the use of mechanical pumps and hence allow simple and reliable measurement of the particle concentration in a space- and energy-saving manner.

The object is achieved in a method of the type stated at the outset by virtue of the fact that the flow of the gas is produced by thermal convection.

The device according to the invention is distinguished by the fact that
(e) the means comprise at least one heat source, which is in thermal contact with the gas and induces thermal convection in the gas by heating the gas.

The essence of the invention consists in partial heating of the gas to be measured to produce thermal convection, which makes the gas flow through the measuring chamber.

According to a first preferred embodiment of the device according to the invention,
(a) the UV light source is surrounded by a radiation absorber which at least partially absorbs the radiation emanating from the UV light source; and
(b) the radiation absorber is arranged on the measuring chamber, in thermal contact with the gas.

Here, the UV light source itself serves as a source for heating the gas.

According to a second preferred embodiment, at least some parts of the electronic measuring unit are used as a heat source.

Further embodiments emerge from the subclaims.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1:
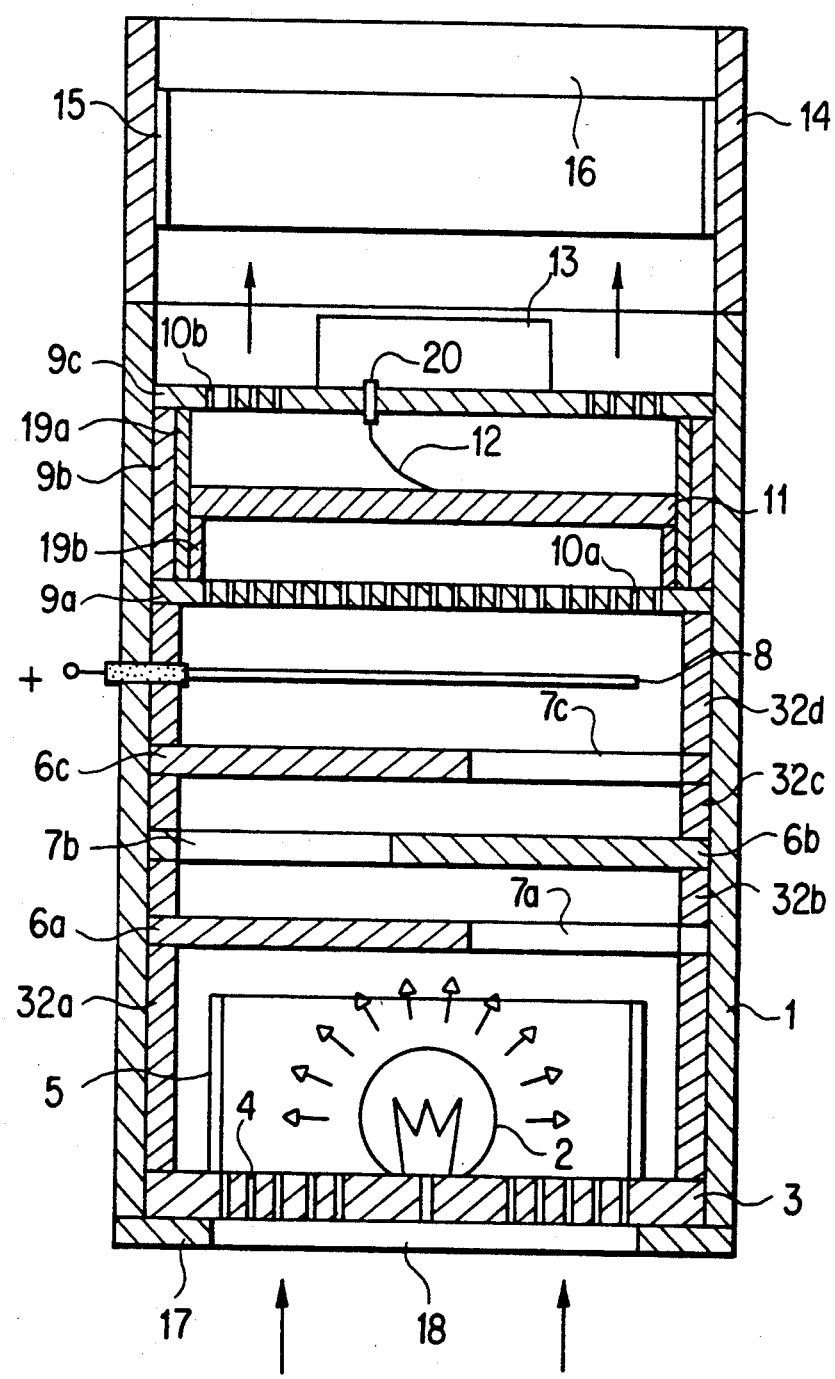
FIG. 1 shows a first preferred illustrative embodiment of a device according to the invention, in which the thermal convection is produced by means of a UV lamp (2) and/or an additional heater (15)

Referring now to the drawings, wherein like reference numerals designate identical or corresponding parts throughout the several views, in FIG. 1 a first preferred illustrative embodiment of a device according to the invention is depicted. The central component of this device is a tubular measurement chamber 1 which contains all the elements essential for measuring the particle concentration.

Arranged at the (bottom) inlet of the measuring chamber 1 is a base plate 3, which is provided with inlet openings 4 and is held in the measuring chamber 1 by an end ring 17 situated underneath it. In its center, the end ring 17 leaves free, as a large opening, a gas inlet 18 through which the gas to be measured with the particles contained in it can pass via the inlet openings 4 in the base plate 3 into the interior of the measuring chamber 1 (indicated by the two arrows).

Mounted centrally on the inner side of the base plate 3 is a UV lamp 2 which emits UV radiation over a large three-dimensional angular range. The gas flowing past the UV lamp 2 is penetrated by the UV radiation and, in the process, those particles in the gas which are carrying PAH are at least partially ionized, i.e. positively charged. In the process of this ionization, electrons are also released. Downstream of the UV lamp 2, the gas, the ionized particles and the electrons flow through a system of several UV screens 6a, 6b and 6c, which have mutually offset screen apertures 7a, 7b and 7c and are arranged in series in a fixed manner by means of corresponding supporting rings 32a, 32b and 32c, into the central part of the measuring chamber 1. The UV screens 6a, 6b and 6c are here intended to prevent an unwanted ionization in the rear part of the measuring chamber 1 due to the UV radiation.

Downstream of the system of UV screens 6a, 6b and 6c, the gas with the ionized particles and electrons contained in it can, for example, be guided past a positively biased electron filter 8 which filters the free electrons present out of the gas stream.

Downstream of the electron filter 8 again is the actual measuring device, which comprises an electrically conducting, gas-permeable ion filter 11. The ion filter 11 is constructed within an electrically conducting Faraday cage, being insulated by means of insulating rings 19a and 19b. The Faraday cage comprises a conducting base plate 9a (with corresponding inlet openings 10a for the gas stream), a conducting side wall 9b and a conducting top plate 9c (with corresponding outlet openings 10b for the gas stream). It is spaced from the screen system (6a, 6b, 6c) underneath it by a further supporting ring 32d. The ion filter 11 is connected via a contact spring 12, which is passed out of the cage via an insulating bushing 20 in the top plate 9c, to an electronic measuring unit 13 mounted outside the cage. The electronic measuring unit measures the current caused by the charged particles caught in the ion filter 11 and is a measure of the PAH concentration.

It is essential for the functioning of the device that a constant stream of gas should be passed through the measuring chamber 1. In the case of the apparatuses known from the prior art, this flow is ensured by a pump, which is arranged either upstream or downstream of the measuring chamber and produces a corresponding positive pressure or vacuum.

The present invention adopts a different solution: the necessary gas flow through the measuring chamber 1 is, in general, set in motion and maintained by thermal convection engendered by local heating of the gas upstream or downstream of the measuring chamber 1. For heating, it is possible to use either heat sources already present in the device (internal) or additionally installed (external) heat sources or a combination of the two. These different variants are represented in the illustrative embodiment in FIG. 1.

A first variant (internal heat source) is based on the fact that a large amount of heat is released in the production of the UV light in the UV lamp 2 due to the relatively poor efficiency. This heat generation is normally an unwanted secondary phenomenon. Given a skillful geometric arrangement, however, this "waste" heat can now be used deliberately to produce a flow of gas or air (chimney effect). For this purpose, it is necessary that the UV lamp 2 should give off as much as possible of the heat generated to the gas stream inside the device. However, since the UV lamp 2 gives off heat primarily in the form of IR radiation, steps must be taken to ensure that the IR radiation is absorbed by surfaces around which the gas to be measured flows. In the device according to FIG. 1, surfaces of this kind are arranged as radiation absorbers 5 around the UV lamp 2.

During operation, the surfaces heat up until a thermal equilibrium is achieved. As a first approximation, the thermal emission of the surfaces of the radiation absorber 5 to the gas flowing past is then equal to the absorbed radiation energy. Any quantity of heat given off to the outside is here unavailable for the production of the gas flow. For this reason, the arrangement must have as small as possible heat losses to the outside, i.e. must be provided with good thermal insulation.

The gas heated by the radiation absorber 5 expands and the pressure difference which arises in the arrangement in the process drives the gas stream (chimney effect). The strength of the gas stream which arises depends primarily on the quantity of heat introduced, the geometry of the arrangement (especially height and cross-section) and on the flow resistance. Since the "chimney height" has a powerful influence on the flow (the flow is approximately proportional to $H^{0.5}$; H=chimney height or length of the tubular gas duct), it is advantageous to increase the gas flow by installing an additional simple extension tube 14 in accordance with FIG. 1. The gas outlet 16 is then correspondingly further away from the gas inlet 18.

Instead of or in addition to the UV lamp 2 as internal heat source, the gas can also be heated up by a heater 15 as an external heat source. Such a heater 15 (preferably in the form of an electrical resistance heater) can, for example, as depicted in FIG. 1, be accommodated in the extension tube 14. Also conceivable, however, is arrangement within or upstream of the gas inlet 18 of the measuring chamber 1.

Figure 2:
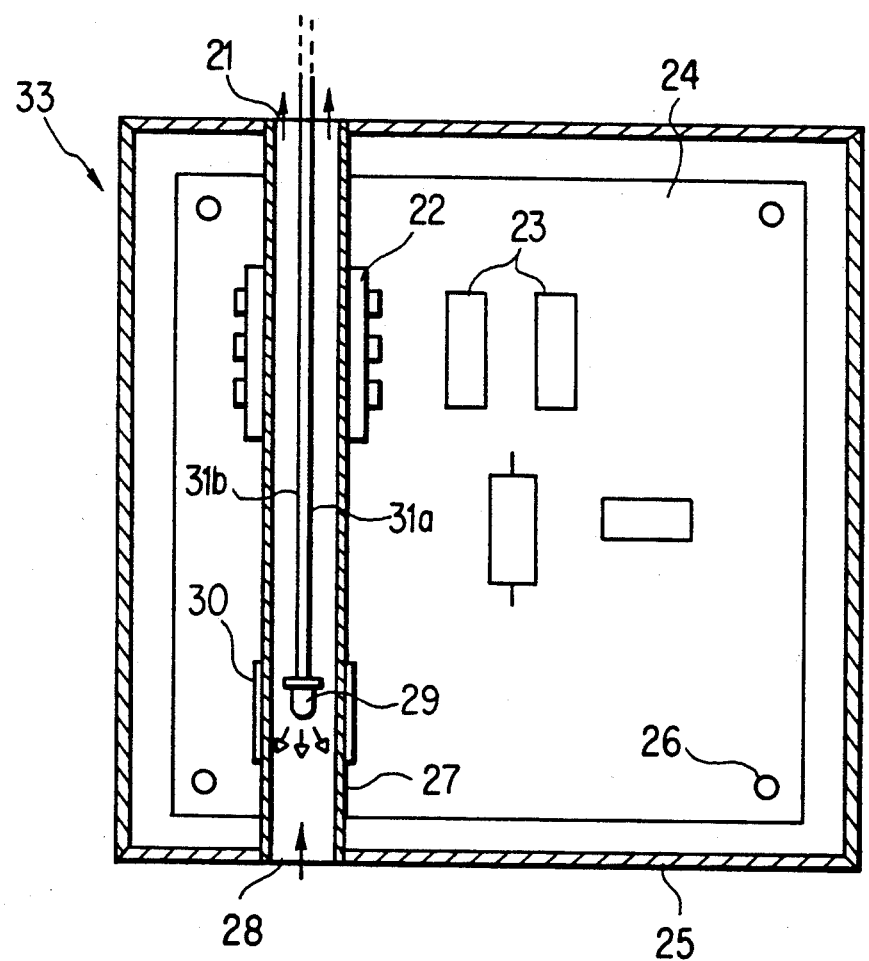
FIG. 2 shows a second preferred illustrative embodiment of a (miniaturized) device according to the invention, in which a miniaturized UV lamp (29) is used as the UV light source and the thermal convection is also produced by parts of the electronic measuring unit (33).

The illustrative embodiment from FIG. 1 represents a measuring instrument which takes up a relatively large amount of space and electrical supply energy. A considerable reduction can be achieved if — as represented in FIG. 2 — the UV lamp is replaced by a miniaturized UV lamp 29 (e.g. a UV-emitting diode) and the ionization section is integrated directly into the electronic measuring unit 33.

Within the electronic measuring unit 33, the individual components 23 and, in particular, a heat-emitting component 22 (in the example depicted an IC) are arranged on a circuit board 24 which, for its part, is fixed in a housing 25 by means of board fixings 26. Running through the housing 25 is glass tube 27, one end of which forms a gas inlet 28 and the other end of which forms a gas outlet 21.

The miniaturized UV lamp 29 is installed in the longitudinal direction within the glass tube 27, in the vicinity of the gas inlet 28, as a UV light source. In so far as the miniaturized UV lamp 29 emits its radiation in a directional fashion, it is arranged in such a way that its direction of radiation is opposed to the direction of flow of the gas to be measured. Because of the directional radiation of the miniaturized UV lamp 29, it is then possible to dispense with the use of UV screens. The lamp supply leads 31a and 31b of the miniaturized UV lamp 29 are passed through the glass tube 27 behind the miniaturized UV lamp 29 over their full length and, given appropriate biasing, can be used directly as an electron filter. The actual ion filter is not depicted in FIG. 2.

In this arrangement too, different methods of heat supply for the thermal convection of the gas can again be provided. A suitable means for this purpose is, on the one hand, a radiation absorber 30, which corresponds in its functioning to the radiation absorber 5 in FIG. 1 and can be applied, for example in the form of an IR-absorbing layer, to the glass tube 27. On the other hand, it is also possible, as an external heat source, to use the electronic circuit itself, in particular the heat-emitting component 22. In this case, the glass tube 27 runs directly over the heat-emitting component 22 — as can be seen in FIG. 2 — and is thermally coupled to the housing of said component.

Overall, a wide choice and wide variation of the type and arrangement of the heat sources is possible within the scope of the invention without losing the specific advantage, namely the reliable production of the gas flow in a space-saving and energy-saving manner.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A method for measuring the concentration of particles present in a gas, comprising the steps of:
    creating a thermally convective flow of gas by use of a UV light source;
    guiding the gas with the particles in the form of a gas stream past the UV light source used to produce the gas flow;
    ionizing the particles by the UV radiation from the UV light source; and
    filtering the ionized particles out of the gas stream and measuring the ionic current which thereby arises.

2. A method as claimed in claim 1, including an additional heat source independent of the UV light source to produce the thermal convection.

3. A device for measuring the concentration of particles present in a gas, comprising:
    a) a tubular measuring chamber through which a gas with particles flows in a flow direction and in the form of a gas stream;
    b) a UV light source positioned at an upstream end of the measuring chamber, past which the gas flows, the particles present in the gas being at least partially ionized thereby;
    c) an electrically conducting ion filter positioned downstream of the UV light source, which filter filters the ionized particles out of the gas stream and releases the electric charges picked up in the process, in the form of an electric current, to a downstream electronic measuring unit; and
    d) means for producing the flow of the gas through the measuring chamber; wherein
    e) the flow producing means comprise at least one heat source, which is in thermal contact with the gas and induces thermal convection in the gas by heating the gas, and
    f) the UV light source comprises one of the heat sources.

4. A device as claimed in claim 3, including
    a) a radiation absorber which at least partially absorbs the radiation emanating from the UV light source, surrounding the UV light source, wherein
    b) the radiation absorber is arranged on the measuring chamber, in thermal contact with the gas.

5. A device as claimed in either of claims 3 and 4, including a heater provided as an additional heat source.

6. A device as claimed in either of claims 3 and 4, including at least some parts of the electronic measuring unit arranged to be used as an additional heat source.

7. A device as claimed in claim 3, wherein:
    a) the UV light source is a UV lamp; including
    b) at least one UV screen arranged downstream of the UV lamp.

8. A device as claimed in claim 3, wherein
    a) the UV light source is a miniaturized UV lamp;
    b) the miniaturized UV lamp is arranged to produce radiation in a direction opposed to the flow direction; and
    c) the UV lamp has supply leads, at least one of the lamp supply leads being used as an electron filter.

9. A device as claimed in claim 3, including an extension tube fitted at at least one end of the measuring chamber in order to improve the flow of gas.

* * * * *